United States Patent
Elder et al.

(10) Patent No.: US 9,879,302 B2
(45) Date of Patent: Jan. 30, 2018

(54) DETERMINING USABILITY OF ANALYTICAL TEST STRIP

(71) Applicant: Cilag GmbH International, Zug (CH)

(72) Inventors: David Elder, Inverness (GB);
Raymond Welsh, Inverness (GB);
David McColl, Inverness (GB);
Prasanta Pati, Aberdeen (GB); Ryan Magennis, Beauly (GB)

(73) Assignee: Cilag GmbH International, Zug (CH)

( * ) Notice: Subject to any disclaimer, the term of this patent is extended or adjusted under 35 U.S.C. 154(b) by 184 days.

(21) Appl. No.: 15/002,552

(22) Filed: Jan. 21, 2016

(65) Prior Publication Data

US 2016/0138075 A1   May 19, 2016

Related U.S. Application Data

(62) Division of application No. 14/139,747, filed on Dec. 23, 2013, now abandoned.

(51) Int. Cl.
*C12Q 1/26* (2006.01)
*G01N 27/327* (2006.01)

(52) U.S. Cl.
CPC .......... *C12Q 1/26* (2013.01); *G01N 27/3272* (2013.01); *G01N 27/3273* (2013.01)

(58) Field of Classification Search
CPC ... C12Q 1/26; G01N 27/3273; G01N 27/3272
See application file for complete search history.

(56) References Cited

U.S. PATENT DOCUMENTS

| | | |
|---|---|---|
| 6,212,417 B1 | 4/2001 | Ikeda et al. |
| 6,444,115 B1 | 9/2002 | Hodges et al. |
| 6,576,102 B1 | 6/2003 | Rappin et al. |
| 6,676,995 B2 | 1/2004 | Dick et al. |
| 6,689,411 B2 | 2/2004 | Dick et al. |

(Continued)

FOREIGN PATENT DOCUMENTS

| | | |
|---|---|---|
| KR | 20120011102 A | 2/2012 |
| KR | 101161322 B1 | 7/2012 |

(Continued)

OTHER PUBLICATIONS

International Search Report and Written Opinion issued in related International Patent Application No. PCT/EP2014/079040, dated Mar. 16, 2015, 10 pages.

*Primary Examiner* — Melanie Yu Brown

(57) ABSTRACT

A system for determining usability of an analytical test strip includes a sample chamber to receive a fluid sample, a reagent in the sample chamber having a moisture-varying impedance, and two detection electrodes contacting the reagent. A test meter applies an AC waveform across the reagent via the detection electrodes while measuring an impedance of the reagent. A processor automatically determines whether the measured impedance of the reagent meets a dryness criterion. The meter includes a housing, a strip port connector, an impedance measurement circuit and the processor. A method for determining usability of a strip inserted in a hand held meter includes applying an AC waveform across a reagent of the strip and measuring a first electrical signal, and determining whether the strip meets the dryness criterion based on the first electrical signal. The test strip and ways of determining an analyte are also described.

1 Claim, 5 Drawing Sheets

(56) References Cited

U.S. PATENT DOCUMENTS

| | | |
|---|---|---|
| 6,749,887 B1 | 6/2004 | Dick et al. |
| 6,830,934 B1 | 12/2004 | Harding et al. |
| 6,866,758 B2 | 3/2005 | Bhullar et al. |
| 7,294,256 B2 | 11/2007 | Happel et al. |
| 8,163,162 B2 | 4/2012 | Chatelier et al. |
| 8,343,331 B2 | 1/2013 | Choi |
| 8,551,320 B2 | 10/2013 | Hodges et al. |
| 8,992,750 B1 | 3/2015 | Beaty et al. |
| 9,128,038 B2 | 9/2015 | Whyte et al. |
| 2004/0120848 A1 | 6/2004 | Teodorczyk |
| 2004/0157337 A1 | 8/2004 | Burke et al. |
| 2005/0114062 A1 | 5/2005 | Davies et al. |
| 2006/0246214 A1 | 11/2006 | Plotkin et al. |
| 2007/0074977 A1 | 4/2007 | Guo et al. |
| 2007/0084734 A1 | 4/2007 | Roberts et al. |
| 2007/0087397 A1 | 4/2007 | Kraft et al. |
| 2007/0102292 A1 | 5/2007 | Dreibholz et al. |
| 2010/0112678 A1 | 5/2010 | Dilleen et al. |
| 2010/0252452 A1 | 10/2010 | Newman et al. |
| 2011/0184264 A1 | 7/2011 | Galasso et al. |
| 2011/0275104 A1 | 11/2011 | Zimmerle et al. |
| 2013/0002278 A1 | 1/2013 | Martin et al. |
| 2013/0002279 A1 | 1/2013 | Martin et al. |
| 2015/0014162 A1 | 1/2015 | Kim et al. |

FOREIGN PATENT DOCUMENTS

| | | |
|---|---|---|
| WO | 9718465 A1 | 5/1997 |
| WO | 2010049669 A1 | 5/2010 |

DETERMINING USABILITY OF ANALYTICAL TEST STRIP

CROSS-REFERENCE

This application is a divisional application of U.S. patent application Ser. No. 14/139,747, filed on Dec. 23, 2013, which the entirety of prior application is hereby incorporated by reference.

TECHNICAL FIELD

The present invention relates, in general, to the field of analyte measurement and, in particular, to test meters and related methods for detecting error conditions of analytical test strips based on specified criteria.

DESCRIPTION OF RELATED ART

The determination (e.g., detection or concentration measurement) of an analyte in a fluid sample is of particular interest in the medical field. For example, it can be desirable to determine glucose, ketone bodies, cholesterol, lipoproteins, triglycerides, acetaminophen or HbA1c concentrations in a sample of a bodily fluid such as urine, blood, plasma or interstitial fluid. Such determinations can be achieved using a hand-held test meter in combination with analytical test strips (e.g., electrochemical-based analytical test strips). Analytical test strips generally include a sample chamber (also referred to herein as an "analyte chamber") for maintaining a liquid analyte, e.g., whole blood, in contact with two or more electrodes. Analytes can then be determined electrochemically using signals conveyed by the electrodes.

Since test meters are used to make care decisions relating to medical conditions, it is desirable that these devices measure with as much accuracy and precision as possible. However, conventional reagents used on analytical test strips can be affected by environmental conditions. For example, a measurement can be affected by the moisture content of the reagent, which is correlated with the relative humidity of the atmosphere around the analytical test strip. It is therefore desirable to measure the effect of humidity to notify a user in advance of obtaining an analyte reading if such an inaccuracy may be present.

BRIEF DESCRIPTION OF THE DRAWINGS

Various novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

DETAILED DESCRIPTION OF ILLUSTRATIVE EMBODIMENTS

Figure 1:
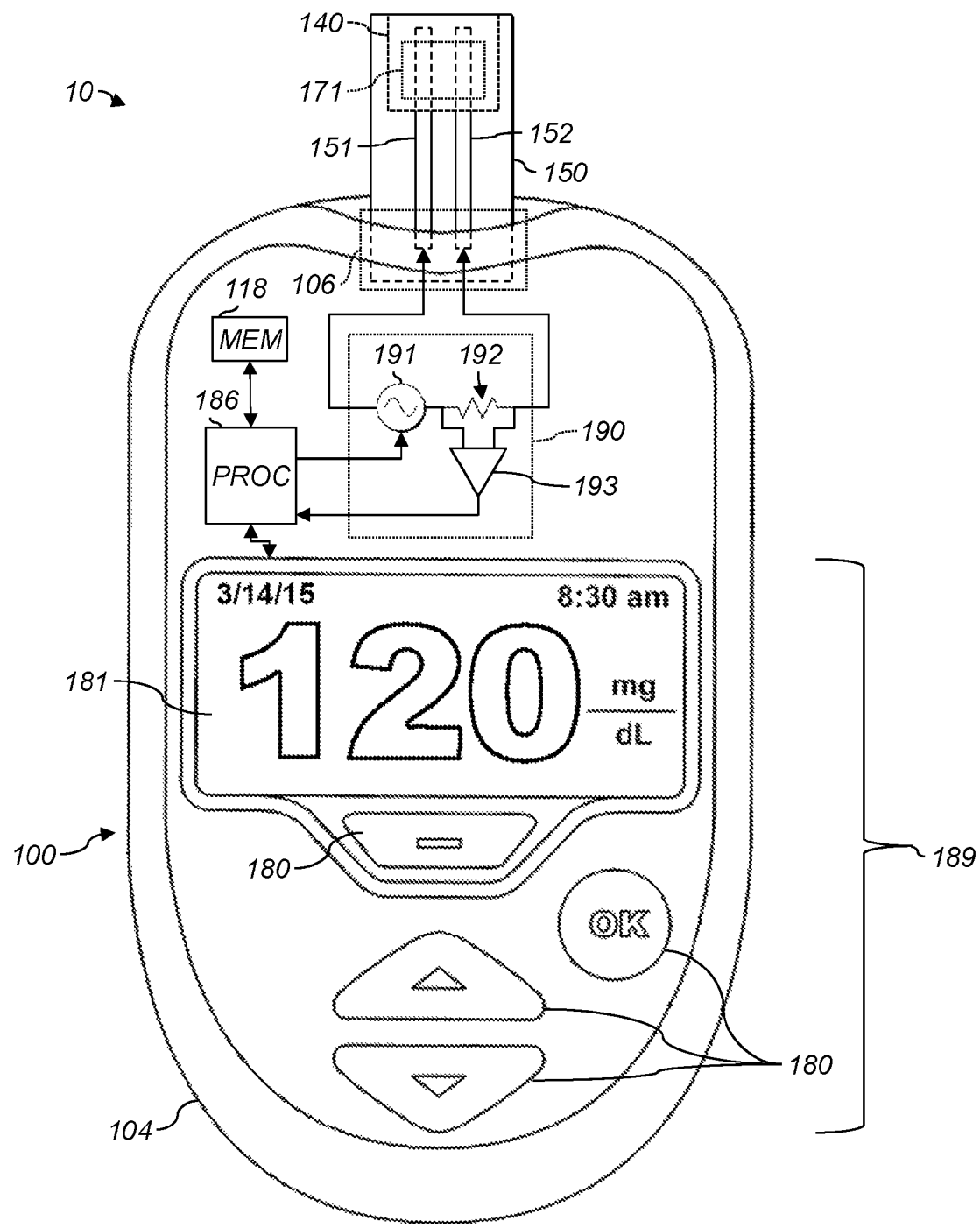
FIG. 1 is a simplified depiction of a system according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, the term "in", as used throughout this description, does not necessarily require that one component or structure be completely contained within another, unless otherwise indicated.

In general, portable test meters, such as hand-held test meters, for use with an analytical test strip in the determination of an analyte (such as glucose) in a bodily-fluid sample (i.e., a whole blood sample) according to embodiments of the present invention include a circuit and a processor configured to apply an AC waveform across a sample chamber of the test strip and measure the impedance of a reagent disposed on the strip while applying the waveform. This permits accurately determining whether reagent moisture is likely to affect an electrochemical measurement taken using the reagent.

Hand-held test meters according to embodiments of the present invention are beneficial in that they provide a qualitative determination of test strip usability. For example, the detection of an unusually low resistance can indicate that the reagent is moist. It is desirable to avoid using such test strips, since the moisture may reduce the accuracy of the results.

A problem solved by various embodiments is to determine the moisture content of a reagent. Various embodiments discussed herein can readily be incorporated by one of sufficient skill into a hand-held test meter. One example of a test meter that can be suitably configured is the commercially available OneTouch® Ultra® 2 glucose meter from LifeScan Inc. (Milpitas, Calif.). Additional examples of hand-held test meters that can also be modified are described in U.S. Patent Application Publication Nos. 2007/0084734 (published on Apr. 19, 2007) and 2007/0087397 (published on Apr. 19, 2007) as well as International Publication Number WO2010/049669 (published on May 6, 2010), incorporated by reference in their entirety.

An experiment was performed to investigate the effect of moisture content on test strips. Control test strips were stored at room temperature in a vial. Experimental test strips were stored in an environmental chamber at 30° C. and 90% relative humidity (RH) for approximately 1.5 hours. Glucose assays were performed using a control solution in each group of test strips. The assay was conducted using a conventional hand-held blood-glucose test meter. The experimental test strips were tested directly after removal from the environmental chamber. The results were as given in Table 1.

TABLE 1

| Assay # | Experiment | Control |
|---|---|---|
| 1 | 389 | 350 |
| 2 | 400 | 361 |
| 3 | 418 | 354 |
| 4 | 413 | 367 |
| 5 | 416 | 355 |
| 6 | 411 | 348 |
| Average | 407.8333 | 355.8333 |

As can be seen, the experimental test strips read significantly higher than the control test strips.

FIG. 1 shows an exemplary system 10 for determining usability of an analytical test strip 150. The system 10 can determine whether the test strip 150 has a reagent 171 that has absorbed moisture. The system 10 includes the analytical test strip 150 having two spaced-apart detection electrodes 151, 152 connected in series with a sample chamber 140. The sample chamber 140 is adapted to receive a fluid sample. The reagent 171 is arranged at least partly in the sample chamber 140, and the detection electrodes 151, 152 are in contact with the reagent 171. The reagent 171 has an impedance that varies with moisture content. An example of the sample chamber 140 is an electrochemical sample cell, as discussed below with reference to FIG. 2. The sample chamber 140 can have a volume ranging, e.g., from about 0.1 microliters to about 5 microliters, or about 0.2 microliters to about 3 microliters, or about 0.3 microliters to about 1 microliter.

The herein described system 10 also includes a test meter 100 adapted to receive the analytical test strip 150. The test meter 100 has an impedance-measurement circuit 190 configured to apply an alternating-current (AC) waveform across the reagent 171 via the detection electrodes 151, 152 and concurrently measure an impedance of the reagent 171. The test meter 100 also includes a processor 186 configured to automatically determine whether the measured impedance of the reagent 171 meets a selected dryness criterion. The selected dryness criterion can be stored, e.g., in a memory block 118.

In at least one example, the selected dryness criterion is an impedance of about 0Ω to about 1 MΩ and the impedance-measurement circuit 190 is configured to apply the AC waveform at a frequency of about 10 kHz, or at a frequency in the range from about 1 kHz to about 100 kHz. The AC waveform can have an amplitude of about 50 mVrms to about 500 mVrms.

In at least one exemplary embodiment, the test meter 100 further includes a user interface 189 including, e.g., a display 181 and one or more user interface buttons 180. In this exemplary embodiment, the processor 186 is configured to, if the measured impedance does not meet the selected dryness criterion, present an error indication via the user interface 189. The error indication can, e.g., request the user to insert a new test strip 150, or request the user to check the package of test strips and make sure it has not expired or been punctured, or inform the user that measurements may have reduced accuracy due to a high moisture level in the reagent 171.

The display 181 can be, for example, a liquid crystal display or a bi-stable display configured to show a screen image. The exemplary screen image shown in FIG. 1 provides indications of glucose concentration ("120") and of date and time ("3/14/15 8:30 am"), as well as a units indication ("mg/dL"). The display 181 can also present error messages or instructions to a user on how to perform a test (analyte determination).

In various embodiments, the impedance-measurement circuit 190 includes a voltage supply, e.g., an AC voltage source 191, configured to apply the alternating-current waveform. The voltage supply can be controlled by the processor 186. In one version, the AC voltage source 191 includes a low-pass filter that receives a square wave from the processor 186 and provides a filtered voltage that is closer to a sinusoid as a result of the filtering. Exemplary low-pass filters for this purpose can include fourth-order filters, multiple feedback low pass filters, and Sallen and Key low pass filters.

The impedance-measurement circuit 190 can further include a transimpedance amplifier configured to detect a current through the reagent while the alternating-current waveform is applied. In the example shown, the AC voltage source 191 is connected to the detection electrode 151. The transimpedance amplifier in the impedance-measurement circuit 190 includes a resistor 192 in series between the detection electrode 152 and the AC voltage source 191. The voltage across the resistor 192 is directly proportional to the current through the AC voltage source 191 and the detection electrodes 151, 152. An amplifier 193 amplifies the voltage across the resistor 192 to provide a voltage signal to the processor 186 that is representative of current through the detection electrodes 151, 152.

As noted, the test meter 100 can be a hand-held test meter for use with an analytical test strip 150 in the determination of at least one analyte in a bodily-fluid sample. Still referring to FIG. 1, the exemplary test meter 100 can include a housing 104 and a strip port connector (SPC) 106 that is configured to receive the analytical test strip 150, which is inserted into a port of the housing 104. The SPC 106 can include spring contacts arranged so that the test strip 150 can be slid into the SPC 106 to electrically connect the spaced-apart detection electrodes 151, 152 of the received analytical test strip 150 with the impedance-measurement circuit 190 or other components of the test meter 100. The SPC 106 can also or alternatively include pogo pins, solder bumps, pin or other receptacles, jacks, or other devices for selectively and removably making electrical connections. The impedance-measurement circuit 190 can thus apply the alternating-current waveform via the SPC 106.

The test meter 100 can also include other electronic components (not shown) for applying test voltages or other electrical signals to the analytical test strip 150, and for measuring an electrochemical response (e.g., plurality of test current values) and determining an analyte based on the electrochemical response. To simplify the present descriptions, the figures do not depict all such electronic circuitry. Exemplary circuits for measuring electrochemical responses are discussed in greater detail in a later portion of this description with reference to FIG. 2.

According to the exemplary embodiment, the processor 186 is disposed within the housing 104. The processor 186 can be adapted to detect the fluid sample in the sample chamber 140 and subsequently cause the impedance-measurement circuit 190 to apply the excitation voltage signal. For the purposes described herein, the processor 186 can include any suitable microcontroller or micro-processor known to those of skill in the art. One exemplary microcontroller is an MSP430F5138 microcontroller that is commercially available from Texas Instruments, Dallas, Tex. USA. The processor 186 can include, e.g., a field-programmable gate array (FPGA) such as an ALTERA CYCLONE FPGA, a digital signal processor (DSP) such as a Texas Instruments TMS320C6747 DSP, or another suitable processing device adapted to carry out various algorithm(s) as described herein, e.g., flowcharts or blocks shown in FIGS. 3 and 5. The processor 186 can include signal-generation and signal-measurement functions, e.g., D/A converters, pulse-train generators, or A/D converters.

Figure 3:
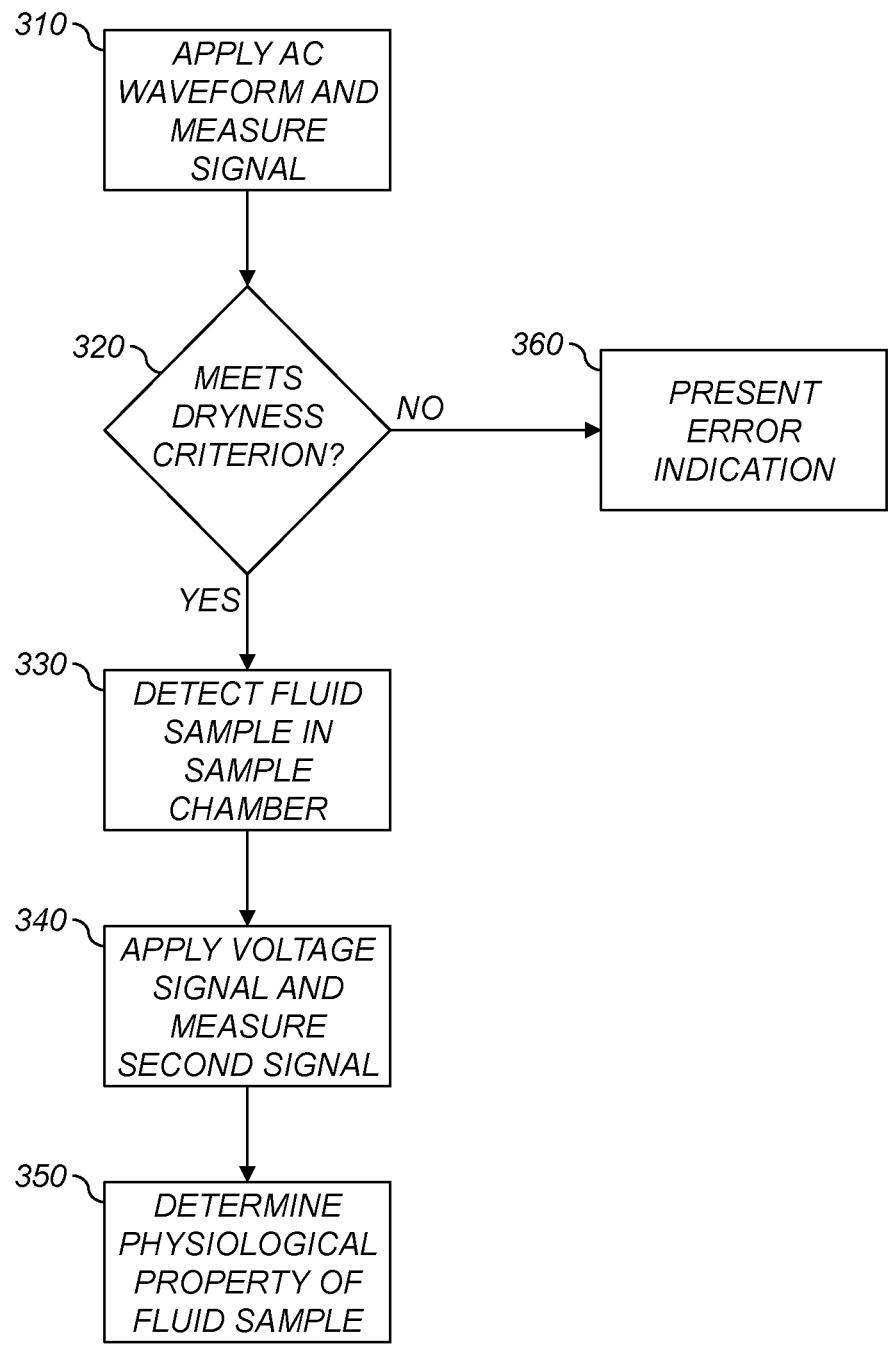
FIG. 3 is a flow diagram depicting stages in an exemplary method for determining usability of an analytical test strip inserted in a hand-held test meter.
Figure 5:
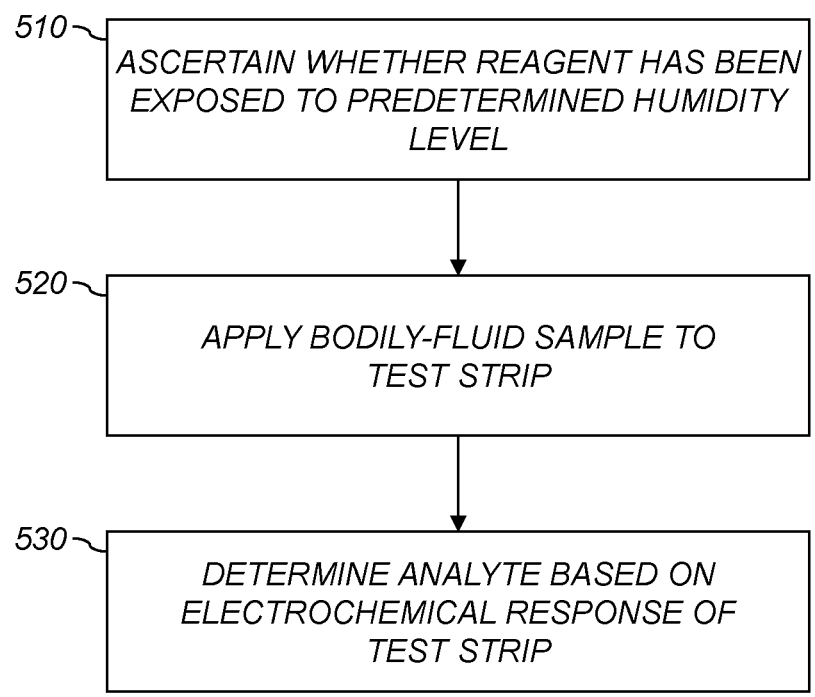
FIG. 5 is a flow diagram depicting stages in an exemplary method for the determination of an analyte in a bodily-fluid sample.

The memory block 118 of the hand-held test meter 100 includes one or more storage device(s), e.g., a code memory (such as random-access memory, RAM, or Flash memory) for storing, e.g., program firmware or software; a data memory (e.g., RAM or fast cache); or a disk (such as a hard drive). Computer program instructions to carry out suitable algorithm(s), e.g., those shown in FIGS. 3 and 5, are stored in one of those device(s). The memory block 118 can also or alternatively be incorporated in the processor 186. A Flash or other nonvolatile memory in the memory block 118 can also contain, e.g., graphics to be displayed on the display 181, text messages to be displayed to a user, calibration data, user settings, or algorithm parameters.

Throughout this description, some embodiments are described in terms that would ordinarily be implemented as software programs. Those skilled in the art will readily recognize that the equivalent of such software can also be constructed in hardware (hard-wired or programmable), firmware, or micro-code. Given the systems and methods as described herein, software or firmware not specifically shown, suggested, or described herein that is useful for implementation of any embodiment is conventional and within the ordinary skill in such arts.

Figure 2:
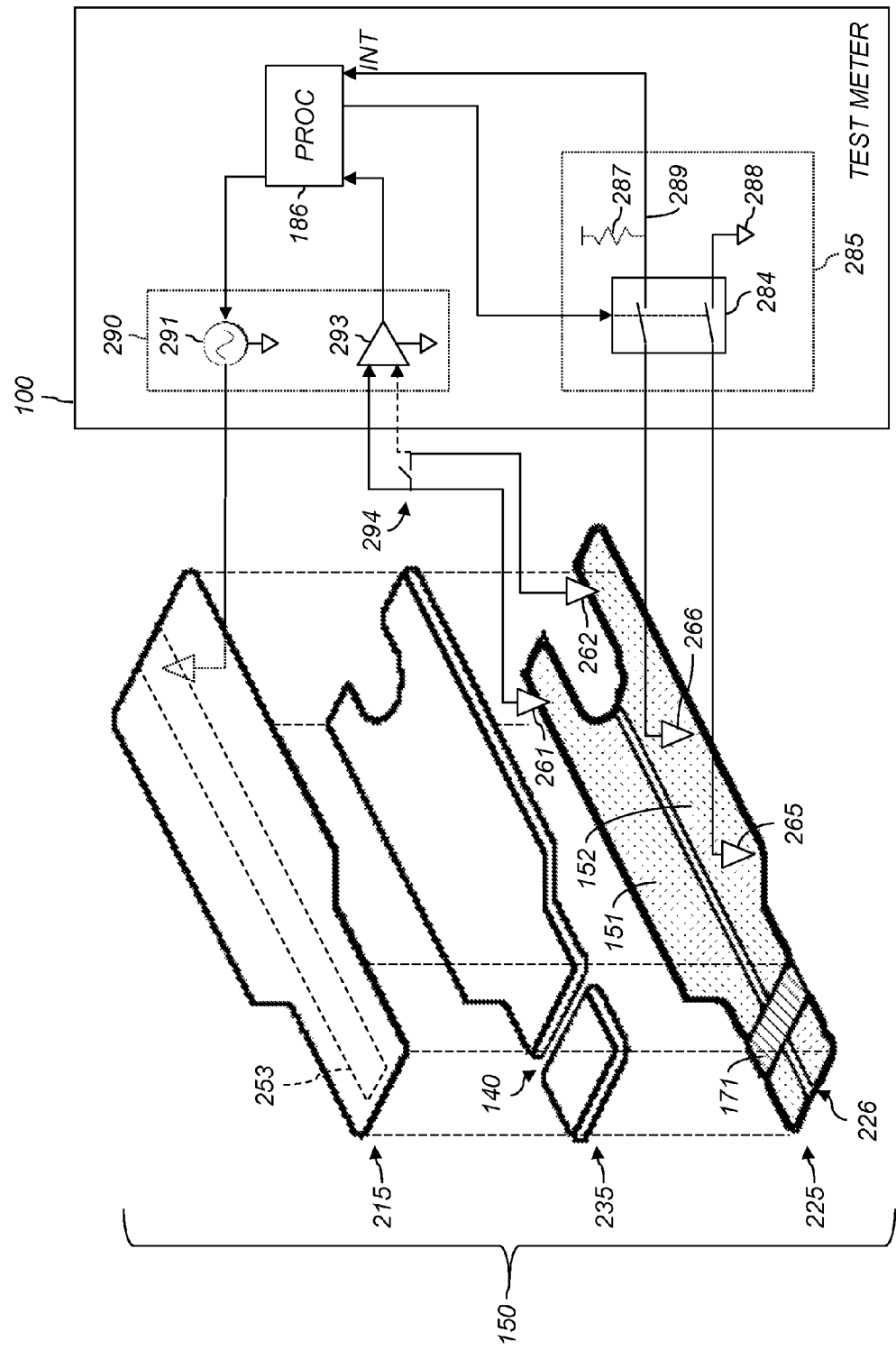
FIG. 2 is an exploded view of an exemplary test strip 150 and a schematic of related components.

FIG. 2 is an exploded view of an exemplary test strip 150 and a schematic of related components. Additional details of various exemplary test strips and measurement methods are provided in US Patent Application Publication No. 2007/0074977 and U.S. Pat. No. 8,163,162, each of which is incorporated herein by reference in its entirety. In the example shown, the exemplary test strip 150 includes a sample electrode 253 arranged at least partly in the sample chamber 140, and the detection electrodes 151, 152. The exemplary sample electrode 253 is electrically insulated from the detection electrodes 151, 152, e.g., by an electrically-insulating spacer 235 arranged between the sample electrode 253 and the detection electrodes 151, 152. The sample chamber 140 can be formed by removing a portion of the spacer 235, or by disposing two separated portions of the spacer 235 between the first and second electrodes 151, 152. In various embodiments, the electrodes 151, 152, 253 can be arranged spaced apart in a facing or opposing faced arrangement, or in other coplanar or non-coplanar configurations. In the example shown, the detection electrodes 151, 152 are laterally adjacent to each other and are arranged on the opposite side of the sample chamber 140 from the sample electrode 253.

In various aspects, the electrodes 151, 152, 253 include conductive thin films formed from materials such as gold, palladium, carbon, silver, platinum, tin oxide, iridium, indium, and combinations thereof (e.g., indium-doped tin oxide or "ITO"). Electrodes can be formed by disposing a conductive material onto electrically-insulating layers 225, 215 by a sputtering, electroless plating, thermal evaporation, or screen printing process. Suitable materials that can be employed in the electrically-insulating layers 215, 225 or the spacer 235 include, for example, plastics (e.g. PET, PETG, polyimide, polycarbonate, or polystyrene), silicon, ceramic, glass, and combinations thereof. In an example, the sample electrode 253 is a sputtered gold electrode disposed over the electrically-insulating layer 215, and the detection electrodes 151, 152 are sputtered palladium electrodes disposed over the electrically-insulating layer 225. The detection electrodes 151, 152 can be deposited separately, or can be formed by, e.g., scribing or etching an isolation channel 226 to separate a deposited film into separate electrodes 151, 152. The isolation channel 226 can be scribed into a gold layer, a palladium layer, or another conductor.

The analytical test strip 150 can be used by a patient or healthcare provider in various ways. For example, once the analytical test strip 150 is interfaced with the hand-held test meter 100, FIG. 1, or prior thereto, a fluid sample (e.g., a whole blood sample or a control-solution sample) can be introduced into the sample chamber 140 of the analytical test strip 150. The analytical test strip 150 can include enzymatic reagents 171 that selectively and quantitatively transform an analyte in the fluid sample into another predetermined chemical form. For example, the analytical test strip 150 can be an electrochemical-based analytical test strip configured for the determination of glucose in a whole blood sample. Such a test strip 150 can include the enzymatic reagent 171 configured in the sample chamber such that the electrochemical response represents a glucose level in the fluid sample. For example, the reagent 171 can include ferricyanide and glucose oxidase so that glucose can be physically transformed into an oxidized form. Movement of charge during this oxidation and related reactions provides a current that can be measured to determine the amount of glucose present in the fluid sample.

Accordingly, in various aspects, the test meter 100 includes an analyte measurement circuit 290. The processor 186 is further configured to, if the measured impedance of the reagent does meet the dryness criterion, detect the presence of the fluid sample in the sample chamber 140 of the received analytical test strip 150. The processor 186 can be further configured to, based upon (e.g., in response to) the detection, operate the analyte measurement circuit to apply a testing waveform across the fluid sample and measure a resulting electrochemical response.

In various embodiments, the analyte measurement circuit 290 is electrically connected to the sample electrode and at least one of the spaced-apart detection electrodes, e.g., via the SPC 106, FIG. 1. In various embodiments, the analyte measurement circuit 290 includes the impedance measurement circuit 190, FIG. 1, or uses components of the impedance measurement circuit 190 such as the AC voltage source 191 and the amplifier 193, both FIG. 1. For example, the AC voltage source 191 or 291 can be shorted or bridged to provide a conductive path between the sample electrode 253 and a reference potential, e.g., ground, during analyte measurement. The analyte measurement circuit 290 can be configured to provide the testing waveform including an AC waveform, a DC level, or a waveform combining AC and DC waveform(s).

In the example shown, a voltage source 291 supplies an AC waveform to the sample electrode 253, e.g., via a contact 263 of the strip port connector 106, FIG. 1. A transimpedance amplifier 293 is connected to one or both of the detection electrodes 151, 152, e.g., via respective contacts 261, 262 of the strip port connector 106. The voltage source 291 can alternatively be connected to the detection electrode(s) 151, 152 and the transimpedance amplifier 293 can be connected to the sample electrode 253. A switch 294 can be provided for selectively shorting the contacts 261, 262. Closing the switch 294 permits a single input to the transimpedance amplifier 293 to be used to measure current traveling through both of the detection electrodes 151, 152.

The processor 186 can operate the voltage source 291 and receive data from the transimpedance amplifier 293. The processor 186 can use information stored in the memory block 118, FIG. 1, in determining an analyte, e.g., in determining a blood glucose concentration, based on the electrochemical response of analytical test strip. For example, the memory block 118 can store calibration tables to adjust for electrical parasitics on the test strip 150.

In at least one exemplary embodiment, the test meter 100 includes two presence-detect contacts 265, 266 configured to electrically contact a selected one of the detection electrodes 151, 152 of the received analytical test strip 150. The test meter 100, or a component thereof (e.g., the impedance-measurement circuit 190), includes a presence-detection circuit 285 configured to detect electrical continuity between the two presence-detect contacts. The processor 186 in this exemplary embodiment is further configured to automatically cause application of the alternating-current waveform subsequent to detection of the electrical continuity. Electrical continuity can be detected when the DC resistance between the presence-detect contacts 265, 266 drops below a selected threshold, e.g., 100Ω. The threshold can be selected based on the resistivity of one or both of the electrodes 151, 152. Although this particular example shows the presence-detect contacts 265, 266 electrically connected through the detection electrode 152, electrical connection can also or alternatively be made through the detection electrode 151, the sample electrode 253, or another electrode or conductive area of the test strip 150.

In an example, the processor 186 is programmed to sleep or otherwise enter a low-power-draw state when the test meter 100 is not in use by a patient. The presence-detection circuit 185 can be connected to an interrupt or wakeup ("INT") pin of the processor 186 to wake up the processor 186 when continuity is detected. When the processor 186 resumes operation, it can test the impedance of the reagent, detect the fluid sample, or perform other processes described herein with respect to the test strip 150.

In the exemplary embodiment shown, the presence-detection circuit 285 includes a pullup resistor 287 (e.g., a resistor wired at one end to a voltage supply) and a current sink 288 (e.g., ground, or a voltage supply with a voltage lower than the voltage of the voltage supply of the pullup resistor 287). A voltage or current source or other circuit for maintaining the voltage of a node within a selected range can be used in place of the pullup resistor 287. A pulldown resistor or circuit and a voltage source can alternatively be used. When electrical continuity is not present between the presence-detect contacts 265, 266, an electrode 289 is held at a relatively higher voltage by the pullup resistor 287. When electrical continuity is present, the electrode 289 is held at a relatively lower voltage by the current sink 288 through the presence-detect contact 265, the electrode 152, and the presence-detect contact 266.

In various aspects, the presence-detection circuit 285 further includes a switch 284 (here, a double-pole, single-throw switch) for selectively electrically isolating at least one of the two presence-detect contacts 265, 266 from the received analytical test strip 150 when open, and the processor 186 is further configured to automatically cause opening of the switch 284 after the impedance of the reagent 171 is measured. This advantageously reduces noise on the analyte measurement that might otherwise be introduced by, e.g., the pullup resistor 287.

In an exemplary aspect for detecting the fluid sample, once a determination is made that the test strip 150 is electrically connected to the test meter 100, the test meter 100 can apply a test potential or current, e.g., a constant current, between the sample electrode 253 and one or both of the detection electrodes 151, 152. In an example, a constant DC current can be applied into the sample chamber 140, and the voltage across the sample chamber 140 can be monitored. When the fluid sample has filled the sample chamber 140, the voltage across the sample chamber 140 will fall below a selected threshold. AC signals, as described herein, can be measured before the sample chamber 140 has filled with fluid, or after the sample chamber 140 has filled with fluid.

The reagent 171 can be disposed within the sample chamber 140 using a process such as slot coating, coating by dispensing liquid from the end of a tube, ink jetting, and screen printing. Such processes are described, for example, in U.S. Pat. Nos. 6,676,995; 6,689,411; 6,749,887; 6,830,934; and 7,291,256; in U.S. Patent Application Publication No. 2004/0120848; and in PCT Application Publication No. WO/1997/018465 and U.S. Pat. No. 6,444,115, each of which is incorporated herein in relevant part by reference. The reagent layer Suitable mediators in the reagent 171 include ferricyanide, ferrocene, ferrocene derivatives, osmium pipyridyl complexes, and quinone derivatives. Suitable enzymes in the reagent 171 include glucose oxidase, glucose dehydrogenase (GDH) based on pyrroloquinoline quinone (PQQ) co-factor, GDH based on nicotinamide adenine dinucleotide (NAD) co-factor, and FAD-based GDH (EC 1.1.99.10).

In at least one example, the electrochemical-based analytical test strip 150 includes an electrically-insulating bottom layer 225. A patterned electrically-conductive layer (e.g., including the detection electrodes 151, 152) is disposed on the electrically insulating bottom layer 225. The patterned electrically-conductive layer includes a first patterned portion (e.g., the detection electrode 151) and a second patterned portion (e.g., the detection electrode 152). An enzymatic reagent layer (e.g., the reagent 171) is disposed on the first patterned portion (e.g., the detection electrode 151), the second patterned portion (e.g., the detection electrode 152) and the electrically-insulating bottom layer 225 such that the enzymatic reagent layer bridges the first patterned portion (e.g., the detection electrode 151) and the second patterned portion (e.g., the detection electrode 152). A patterned spacer layer (e.g., the spacer 235) is arranged over the patterned electrically-conductive layer. A top electrically conductive layer (e.g., the sample electrode 253) is arranged over the spacer 235. An electrically-insulating top layer 215 is arranged over the top electrically conductive layer (e.g., the sample electrode 253). The terms "top" and "bottom" do not constrain the orientation of the test strip 150 during manufacturing or use, but are used for clarity of explanation.

FIG. 3 is a flow diagram depicting stages in a method for determining usability of an analytical test strip inserted in a hand-held test meter. The steps can be performed in any order except when otherwise specified, or when data from an earlier step is used in a later step. In at least one example, processing begins with step 310. For clarity of explanation, reference is herein made to various components shown in FIGS. 1 and 2 that can carry out or participate in the steps of exemplary method(s). It should be noted, however, that other components can be used; that is, exemplary method(s) shown in FIG. 2 are not limited to being carried out by the identified components. An exemplary method includes performing below-described steps using the processor 186 and at least one electrical circuit of the test meter, e.g., the impedance-measurement circuit 190.

In step 310, an alternating-current waveform is applied across a reagent 171 of the inserted analytical test strip 150 and a first electrical signal is measured. This can be performed by the processor 186 commanding and receiving data from the impedance-measurement circuit 190, as discussed above with reference to FIGS. 1 and 2.

In decision step 320, the processor 186 determines whether the inserted analytical test strip 150 meets a selected dryness criterion based on the first electrical signal. This can be as discussed above. If so, step 330 is next. If not, step 360 is next.

In step 330, the inserted analytical test strip 150 meets the selected dryness criterion. A fluid sample is detected in a sample chamber of the inserted analytical test strip. This can be done, e.g., by applying a constant current across the sample chamber 140 as described above, or in other ways. Step 340 is next.

In step 340, a voltage signal is applied across the detected fluid sample in the sample chamber and a second electrical signal is measured. The second electrical signal is mediated by the reagent. Examples are given above with respect to oxidation of glucose. Step 350 is next.

In step 350, a physiological property of the fluid sample, e.g., blood glucose level or hematocrit, is determined using the second electrical signal. The physiological property can be determined using, e.g., the change in phase or magnitude from the voltage signal to the second electrical signal. As discussed above, in various aspects, the reagent is configured so that the second electrical signal represents a blood glucose level in the fluid sample.

If the measured impedance does not meet the selected dryness criterion, decision step 320 is followed by step 360. In step 360, the processor 186 automatically presents an error indication via the user interface 189. Step 360 can include automatically computing or rendering a visual representation of the error indication and displaying the visual representation on the display 181, FIG. 1.

Figure 4A:
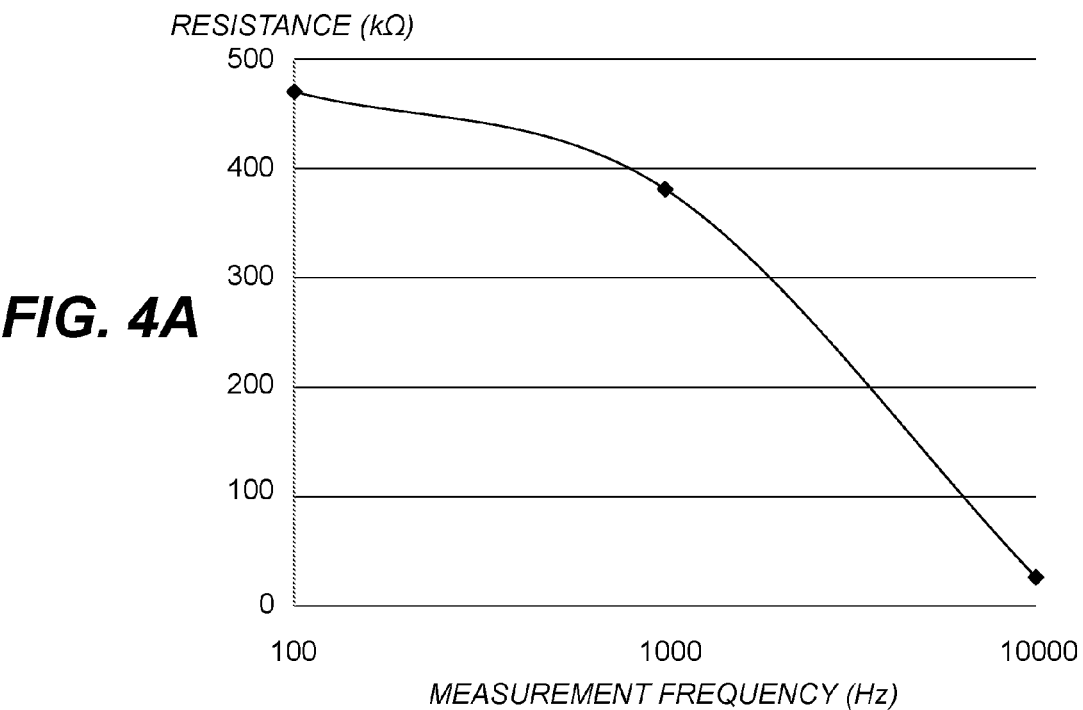
FIGS. 4A and 4B show experimental data of a tested analytical test strip with a reagent.
Figure 4B:
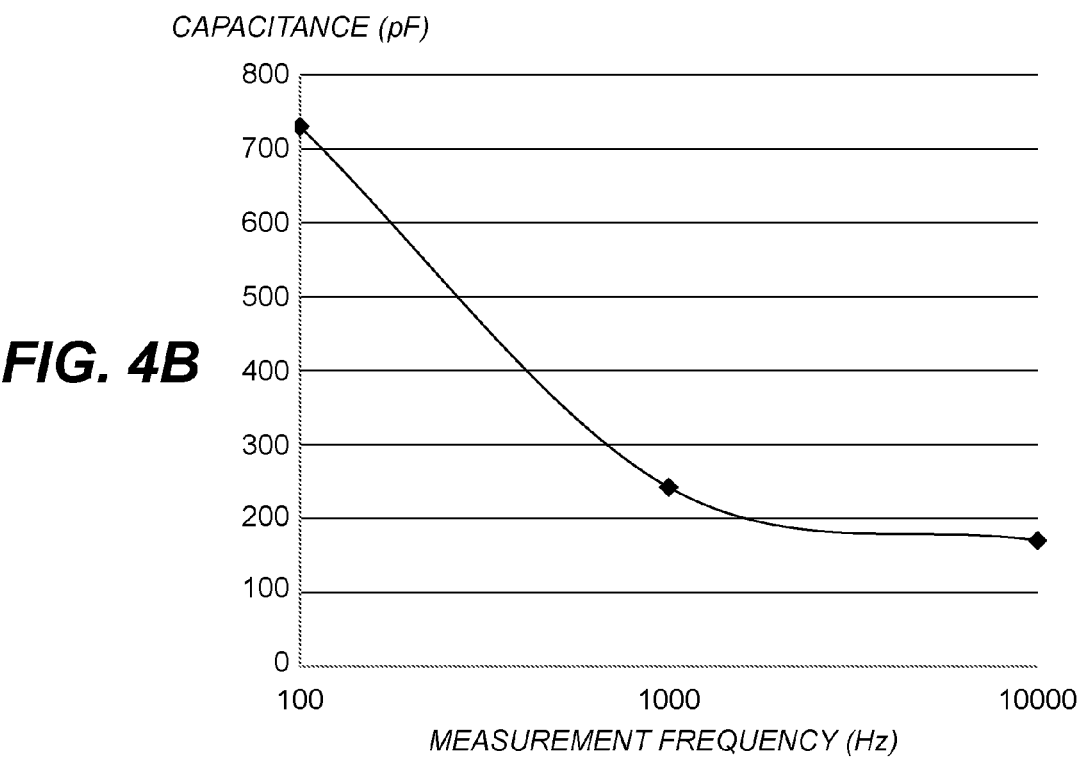

FIGS. 4A and 4B show experimental data of a tested analytical test strip 150 with a reagent 171. FIG. 4A shows measured resistance in kΩ as a function of measurement frequency in Hz. FIG. 4B shows measured capacitance in pF as a function of measurement frequency (Hz). The tests that produced the illustrated results were carried out in a thermal chamber at 30° C. and 90% RH. At DC, the resistance (not shown in FIG. 4A) was 10 MΩ. As measurement frequency increased, the moist test strip 150 showed a decrease of resistance (FIG. 4A) and a decrease of capacitance (FIG. 4B). In this example, both resistance and capacitance have significantly reduced values at 10 kHz compared to 100 Hz. Subsequent measurements outside the 90% RH condition demonstrated that AC impedance rose as the strip dried out.

For comparison, tests were performed at lower RH levels. Tests were also performed on a control test strip that did not have a reagent. At an RH of 80%, both of the test strips 150 (with and without reagent) showed a resistance of approx 6 MΩ at 10 kHz. At an RH below 80%, the experimental test strip 150 showed resistance above the limit of the ohmmeter and approx 156 pF capacitance. This capacitance was determined to be the result of the test setup.

Characterization measurements similar to those shown in FIGS. 4A and 4B can be collected and processed or analyzed to determine the dryness criterion and alternating-current waveform frequency for a selected design of the test strip 150. The threshold can be chosen according to the resistivity of the detection electrodes 151, 152. In an example, the threshold can be higher for detection electrodes 151, 152 including carbon conductors than for detection electrodes 151, 152 including sputtered Pd conductors. In some aspects, the geometry of the sample chamber 140 and the reagent 171 are constrained by the analyte measurement to be performed. The threshold can be selected for the test strip 150 conforming to those constraints on geometry. In various aspects, the geometry of the test strip 150 can be selected to provide desired thresholds. For example, the width of the isolation channel 226 can be selected wider to increase AC impedance or narrower to decrease AC impedance.

FIG. 5 is a flow diagram depicting stages in an exemplary method for the determination of an analyte in a bodily-fluid sample. The steps can be performed in any order, with exceptions noted above. In at least one example, processing begins with step 510. As discussed above, various components can be used in carrying out the exemplary method. The below-described steps can be carried out using the processor 186 and at least one electrical circuit of the test meter, e.g., the impedance-measurement circuit 190.

In step 510, it is ascertained whether an enzymatic reagent layer of an electrochemical-based analytical test strip has been exposed to a predetermined humidity level by measuring an electrical characteristic of the enzymatic reagent layer. As discussed above, in at least one example the electrochemical-based analytical test strip has an electrically-insulating bottom layer; a patterned electrically-conductive layer disposed on the electrically insulating bottom layer and including a first patterned portion and a second patterned portion; an enzymatic reagent layer disposed on the first patterned portion, the second patterned portion and the electrically-insulating bottom layer such that the enzymatic reagent layer bridges the first patterned portion and the second patterned portion; a patterned spacer layer; a top electrically conductive layer; and an electrically-insulating top layer.

In step 520, the bodily-fluid sample is applied to the electrochemical-based analytical test strip. For example, the sample chamber 140 can be filled with the bodily-fluid sample.

In step 530, the analyte (e.g., blood glucose level, or another physiological property) is determined based on an electrochemical response of the electrochemical-based analytical test strip. The electrochemical response can be mediated by the reagent 171. The analyte can be determined, e.g., by measuring a current through the sample electrode 253 and one or both of the detection electrodes 151, 152 as the analyte reacts with the reagent 171. Other ways of determining analytes are described, e.g., in the above-referenced patent documents. Analyte determination can be performed, e.g., using AC, DC, or combined waveforms; by applying voltages or currents; and by measuring currents, voltages, or impedances, any of which can be real- or complex-valued. For example, an AC excitation waveform can be applied across the sample chamber 140 and AC measurements can be taken at one or more signal phase(s) with respect to the AC excitation waveform.

Using various methods, devices or systems described herein advantageously permits determining moisture content of the reagent 171 on the analytical test strip 150, FIG. 1. Various aspects permit notifying the user before a measurement is taken using a test strip that may be inaccurate due to the moisture content of the reagent 171. Technical effects of various aspects including transducing moisture content into an electrical signal; quantitatively transforming an analyte in the fluid sample into another predetermined chemical form; carrying out an electrochemical reaction to permit measuring the analyte in the fluid sample; and computing and presenting visible representations informing a user that the test strip 150 is too moist.

PARTS LIST FOR FIGS. 1-5

10 system
100 test meter
104 housing
106 strip port connector (SPC)
118 memory block
140 sample chamber
150 analytical test strip
151, 152 detection electrodes
171 reagent
180 user interface button
181 display
185 presence-detection circuit
186 processor
189 user interface
190 impedance-measurement circuit
191 AC voltage source
192 resistor
193 amplifier
215, 225 electrically-insulating layers
226 isolation channel
235 spacer
253 sample electrode
261, 262, 263 contacts
265, 266 presence-detect contacts
284 switch
285 presence-detection circuit
287 pullup resistor
288 a current sink
289 electrode
290 analyte measurement circuit
291 voltage source
293 transimpedance amplifier
294 switch
310 step
320 decision step
330, 340, 350, 360 steps
510, 520, 530 steps While preferred embodiments of the present invention have been shown and described herein, it will be obvious to those skilled in the art that such embodiments are provided in this description by way of example only. To that end, numerous variations, changes, and substitutions will be readily apparent to those skilled in the art without departing from the invention. In addition, it should be understood that various alternatives to the embodiments of the invention described herein can be employed in practicing the invention. References to "a particular embodiment" (or "aspect") and the like refer to features that are present in at least one embodiment of the invention. Separate references to "an embodiment" (or "aspect") or "particular embodiments" or the like, however, do not necessarily refer to the same embodiment or embodiments; however, such embodiments are not mutually exclusive, unless specifically indicated or as are readily apparent to one of skill in the art. The word "or" is used in this disclosure in a non-exclusive sense, unless otherwise explicitly noted. It is intended that the following claims define the scope of the invention and that devices and methods within the scope of these claims and their equivalents be covered thereby.

What is claimed is:

1. A method for the determination of an analyte in a bodily-fluid sample, the method comprising:
   ascertaining whether an enzymatic reagent layer of an electrochemical-based analytical test strip has been exposed to a predetermined humidity level by measuring an electrical characteristic of the enzymatic reagent layer, the electrochemical-based analytical test strip having:
      an electrically-insulating bottom layer;
      a patterned electrically-conductive layer disposed on the electrically insulating bottom layer and including a first patterned portion and a second patterned portion;
      an enzymatic reagent layer disposed on the first patterned portion, the second patterned portion and the electrically-insulating bottom layer such that the enzymatic reagent layer bridges the first patterned portion and the second patterned portion;
      a patterned spacer layer;
      a top electrically conductive layer; and
      an electrically-insulating top layer;
   applying the bodily-fluid sample to the electrochemical-based analytical test strip; and
   determining the analyte based on an electrochemical response of the electrochemical-based analytical test strip.

* * * * *